United States Patent [19]

Caskey

[11] Patent Number: 4,970,332

[45] Date of Patent: Nov. 13, 1990

[54] PROCESS FOR PRODUCING 2-ETHYLHEXYL-P-METHOXYCINNAMATE

[75] Inventor: Douglas C. Caskey, O'Fallon, Mo.

[73] Assignee: Mallinckrodt, Inc., St. Louis, Mo.

[21] Appl. No.: 321,273

[22] Filed: Mar. 9, 1989

[51] Int. Cl.[5] .............................................. C07C 69/76
[52] U.S. Cl. ........................................ 560/104; 560/55
[58] Field of Search ................................... 560/104, 55

[56] References Cited

U.S. PATENT DOCUMENTS

| | | | |
|---|---|---|---|
| 3,700,727 | 10/1972 | Heck | 260/476 R |
| 3,705,919 | 12/1972 | Heck | 260/491 |
| 4,578,507 | 3/1986 | Wada et al. | 560/104 |
| 4,592,906 | 6/1986 | Baker | 424/60 |
| 4,618,698 | 10/1986 | Beitzke | 560/60 |
| 4,620,027 | 10/1986 | Hsu | 560/104 |
| 4,737,591 | 4/1988 | Hsu | 560/104 |

OTHER PUBLICATIONS

Heck, et al., *J. Org. Chem.*, 37(14):2320 (1972).
Patel, et al., *J. Org. Chem.*, 42(24):3903 (1977).
Mori, et al., *Bull. Chem. Soc. of Japan*, 46:1505–1508 (1973).

*Primary Examiner*—Paul J. Killos
*Attorney, Agent, or Firm*—Bernard, Rothwell & Brown

[57] ABSTRACT

A process for producing cinnamates comprising reacting an iodobenzene compound with an acrylate ester in the presence of trialkylamine and a catalyst comprising palladium on a support. In one embodiment, 2-ethylhexyl-p-methoxycinnamate is produced by the process comprising diazotizing p-anisidine to produce a diazotization product and reacting the diazotization product with an aqueous iodide solution to produce 4-iodoanisole, reacting the 4-iodoanisole product with 2-ethylhexylacrylate in the presence of trialkylamine and a catalyst comprising palladium on a support to produce 2-ethylhexyl-p-methoxycinnamate and a trialkylamine-hydroiodide salt and then recovering iodide and trialkylamine from the trialkylamine-hydroiodide salt by reacting the salt with an alkali hydroxide.

7 Claims, No Drawings

PROCESS FOR PRODUCING 2-ETHYLHEXYL-P-METHOXYCINNAMATE

FIELD OF THE INVENTION

The present invention relates to the production of cinnamates for use as sunblocking agents.

BACKGROUND OF THE INVENTION

It is well-established in the chemical literature that aryl halides react with alkenes under the influence of palladium catalysts to form vinylically substituted products. In general, these reactions are performed using aryl bromides as the source of the aryl moiety since bromides are substantially more economical than the corresponding iodides. For example, Patel et al., *J. Orc. Chem.*, 42(24):3903 (1977), describes palladium-catalyzed vinylic substitution reactions with carboxylic acid derivatives. Bromobenzoic acids are reacted with vinylic compounds in the presence of triethylamine with palladium acetate and tri-o-tolylphosphine as the catalyst. Unfortunately, the bromides do not react as fast and clean as the iodides, making reactions using iodides more attractive than those using bromides. Iodides, however, have been considered too expensive for most applications.

These reactions generally are performed using soluble, homogeneous organopalladium species, usually beginning with palladium acetate, Pd(OAc)$_2$. In one literature article, *Bull, Chem. Soc. Japan*, 46:1505–1508 (1973), it is mentioned that palladium black can be used effectively. In this article, methanol is used as the reaction solvent at a reaction temperature of 120–125° C. Because of these harsh conditions, use of this method results in the undesirable necessity of using pressure vessels, which detracts from the practical utility of the method.

Heck et al., *J. Org. Chem.*, 37(14):2320 (1972), describes palladium-catalyzed vinylic hydrogen substitution reactions with aryl, benzyl, and styryl halides. One of the reactions tried by Heck was the reaction of 4-iodoanisole with methylacrylate in the presence of a palladium catalyst to form methyl-p-methoxycinnamate. The preferred palladium catalyst was an in situ palladium acetate reduction catalyst. The yield for this reaction was a rather low 68%. Further, the use of the homogeneous palladium catalyst is expensive since these catalysts are not easily recovered and rejuvenated for further use. Although the Heck article states that a palladium on carbon catalyst may be used, the authors state that these reactions are slower and the yields lower than with the homogeneous catalysts.

Thus, there is a need in the art for an economical method for producing high yields of cinnamates. Further, there is a need for a process which utilizes a catalyst which can be easily recovered and inexpensively used.

SUMMARY OF THE INVENTION

We unexpectedly have discovered that cinnamates can be produced economically and efficiently by the process comprising reacting an iodobenzene compound with an acrylate ester in the presence of trialkylamine and a catalyst comprising palladium on a support. In one embodiment, 2-ethylhexyl-p-methoxinnamate is produced by the process comprising first diazotizing p-anisidine to produce a diazotization product and reacting the diazotization product with an aqueous iodide solution to produce 4-iodoanisole. Then, the 4-iodoanisole product is reacted with 2-ethylhexylacrylate in the presence of trialkylamine and a catalyst comprising palladium on a support to produce 2-ethylhexyl-p-methoxycinnamate and a trialkylaminehydroiodide salt. The iodide and trialkylamine are recovered from the trialkylamine-hydroiodide salt by reacting the salt with an alkali hydroxide.

DETAILED DESCRIPTION OF THE INVENTION

In accordance with the present invention, a process for producing cinnamates has been discovered wherein an iodobenzene is reacted with an acrylate ester in the presence of trialkylamine and a catalyst comprising palladium on a support. This process provides for the use of an easily recoverable catalyst since palladium on a support may be recovered by a simple filtration using methods well-known in the art. Further, this reaction utilizes iodide compounds which result in faster, cleaner reactions and allows for recovery and recycle of the iodide compounds to foster efficiency and economy.

The cinnamates which are produced by the method of this invention have the structure

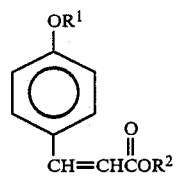

wherein R$^1$ is lower alkyl of 1–4 carbon atoms and R$^2$ is a branched or unbranched, substituted or unsubstituted alkyl group containing about 4 to about 20 carbon atoms. Acrylate esters which may be used in the process of this invention to produce cinnamates include acrylate esters which contain 4 or more carbon atoms in the alkyl portion of the ester such as CH$^2$—CHCOOR$^2$. The carbon chain may be straight or branched and may contain hetero atoms. Examples of acrylate esters which can be reacted with an iodobenzene to produce desired cinnamates include amyl acrylate, 2-ethoxyethyl acrylate and 2-ethylhexyl acrylate. The most preferred acrylate ester for the process of this invention is 2-ethylhexyl acrylate.

The iodobenzene which can be used in the process of this invention includes any substituted or unsubstituted iodobenzene Preferably, the iodobenzene is substituted at the 4- position with a lower alkoxy. In the most preferred embodiment, the iodobenzene is 4-iodoanisole, which is a substituted iodobenzene with methoxy at the 4- position.

The trialkylamine may be any amine wherein the alkyl portion has between about one and about six carbon atoms. In the preferred embodiment described here, the trialkylamine is triethylamine.

The palladium catalyst used in the process may be any supported palladium catalyst. Supports which may be used in the process of this invention include barium sulfate, alumina, kieselguhr and carbon, among others. A preferred support for the palladium catalyst is carbon, which is preferred due to its ready availability, ease of handling and ease of metal recovery. Unsupported palladium such as palladium black may be used, but is less desirable since it is not as efficient on a weight of palladium basis. Homogenous palladium catalysts such as palladium acetate, palladium bis-dibenzylideneacetone, among others, work in the process of the invention but are not easily recoverable or recyclable.

In a preferred embodiment, carbon is used as the support and is loaded with between about 0.25% and about 20% palladium. The catalyst which is used in the most preferred embodiment is a 5% palladium on carbon catalyst in a dry form.

The process of this invention is most preferably used to produce 2-ethylhexyl-p-methoxycinnamate for use as a sunscreen.

The reaction for the production of 2-ethylhexyl-p-methoxycinnamate may be illustrated as follows:

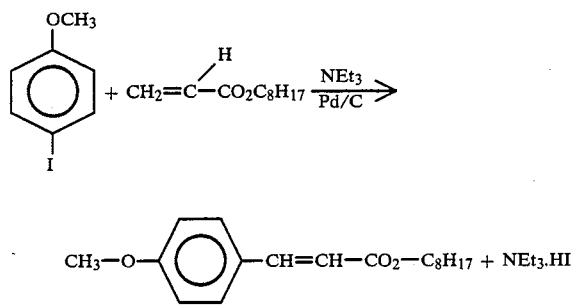

In one embodiment of the present invention, 4-iodoanisole, 2-ethylhexylacrylate, trialkylamine and a palladium on a support catalyst are charged to a reaction vessel. The 4-iodoanisole employed in this process is preferably in a molten form.

The mixture of 4-iodoanisole, 2-ethylhexylacrylate and trialkylamine charged to the reaction vessel is heated with stirring. The mixture first is heated to about 100° to 105° C. to reflux. The reflux temperature will gradually increase to about 140° C. The reaction above 100° C. will generally continue for between about two to about four hours. After the reaction is complete, as determined by gas chromatography or by another method known to those skilled in the art, the reaction mixture is cooled to between about 25° C. to about 30° C. The palladium catalyst and the trialkylamine-hydroiodide salt then are recovered from the solution by a simple filtration step, leaving a filtered product solution. The filtered product is washed to remove any soluble salt. The resulting phases are allowed to separate until the top organic product phase is ready for distillation. After distillation, the distilled product is 2-ethylhexyl-p-methoxycinnamate. Distillation may be carried out by any of the known methods of distillation. The remaining aqueous phase which contains a trialkylaminehydroiodide salt, may be processed further to recover trialkylamine and iodide. This procedure can be followed with other acrylate ester reactants to produce other desired cinnamates.

In a preferred embodiment of this invention, the 4-iodoanisole used in the production of 2-ethylhexyl-p-methoxycinnamate is prepared by the following reaction:

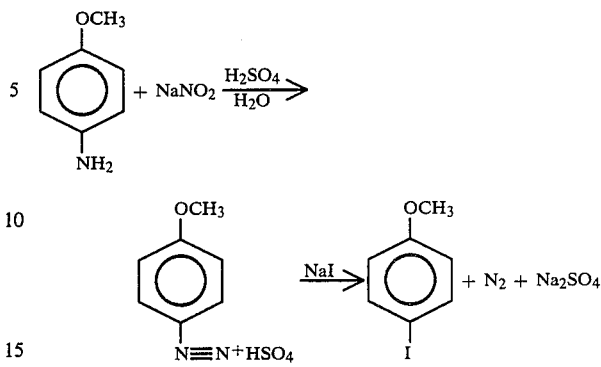

This diazotization reaction has been described in the literature; for example, in Blicke et al., *J. Am. Chem. Soc.*, 50:1231 (1928) or Matheson et al., *J. Chem. Soc.*, p. 1106 (1931).

Water and p-anisidine are charged to a reaction vessel and the mixture of water and p-anisidine is stirred while concentrated acid is added slowly. The preferred acid is 98% sulfuric acid. Stirring is continued for between about 20 and 30 minutes. The mixture then is cooled to between about 0° and 5° C. While the temperature is maintained at between about 0° and 6° C., a solution of sodium nitrite and water is added to the solution to diazotize the p-anisidine. The addition is conducted over a time span of between about one and a half (1½) to two (2) hours. The resulting diazo solution may be filtered to remove any solid or tarry material. Optionally, urea may be added to the filtered diazo solution to remove excess nitrous acid.

In another reaction vessel, a solution of iodide, preferably an alkali iodide, and water is prepared and the temperature is adjusted to between about 25° and 35° C. In the preferred embodiment, the iodide used for the process of this invention is sodium iodide. The filtered diazo solution is slowly added to the iodide solution and stirred at between about 25° and 35° C. for between about 4 to about 12 hours. After stirring, the reaction mixture is heated to between about 50° and 55° C. Then, a base is added until the pH is between about 7.5 to 8.0. The preferred base is 50% sodium hydroxide. Once the phases have separated, the product layer containing 4-iodoanisole will be on the bottom. This organic phase is collected and washed with water at a temperature of between about 65° to 70° C. When the phases again have separated, the aqueous phase is discarded. The resulting product is molten 4-iodoanisole, which may be reacted with 2-ethylhexylacrylate to produce 2-ethylhexyl-p-methoxycinnamate.

A by-product of the reaction for the production of 2-ethylhexyl-p-methoxycinnamate is a trialkylaminehydroiodide salt. The process of this invention provides a convenient procedure for recycling the iodide and trialkylamine, making the process more economical and more efficient than previously tried processes for the production of cinnamates. Further, iodides are preferred in aryl halide reactions with alkenes under the influence of palladium catalysts, although they heretofore have been viewed as too expensive to use. The iodide and trialkylamine may be recovered from the aqueous phase resulting from the distillation step of the preparation of 2-ethylhexyl-p-methoxycinnamate. While the organic phase is distilled to obtain 2-ethylhexyl-p-methoxycinnamate, the aqueous phase may be recovered and further processed.

The recovery of the iodide may be illustrated by the following reaction equation:

$$NEt_3 \cdot HI + NaOH \rightarrow NaI + NEt_3 + H_2O$$

In a preferred embodiment, the bottom aqueous phase from the production of 2-ethylhexyl-p-methoxycinnamate first is heated to between about 80° to 85° C. and then is recycled through the filter containing the palladium catalyst and trialkylaminehydroiodide salt resulting from the filtration step of the production of 2-ethylhexyl-p-methoxycinnamate. The recycling is continued until all the salt is dissolved. The palladium catalyst will be left on the filter to be recycled to the next reaction. The resulting solution will separate into two phases. The aqueous phase is allowed to settle before the top organic phase is collected and combined with the filtered product from the process of producing the 2-ethylhexyl-p-methoxycinnamate. The remaining aqueous phase is cooled to between about 65° and 70° C. and a base is added until the pH is about 9.5 or greater. The preferred base is an alkali hydroxide, most preferably, 50% NaOH. After the pH is adjusted, the temperature is adjusted to about 70° C. The phases will separate and the top trialkylamine phase may be recycled to the process for preparing 2-ethylhexyl-p-mathoxycinnamate while the bottom iodide solution phase may be recycled to the process for preparing the iodoanisole.

The yield of 2-ethylhexyl-p-methoxycinnamate in the process of the present invention is above about 90%. This is in contrast to the 68% yield reported by Heck et al. in the article described above, in which a homogeneous palladium catalyst was employed to produce methyl-p-methoxycinnamate. Although not wishing to be bound by any theory, it is believed that the interaction of the palladium catalyst and the 2-ethylhexyl ester as opposed to the methyl ester and soluble palladium catalyst of the literature reference, causes this beneficial, unexpected result. A possible explanation of why the reaction yield is so much higher with the process of this invention is that there is a very high affinity of the 2-ethylhexyl acrylate for the carbon support of the palladium on carbon support catalyst. Both species are very nonpolar and hydrophobic and the hydrophobic 2-ethylhexyl chain tends to absorb in the carbon matrix, expediting the reaction of the acrylate function with the palladium surface. By contrast, the methyl function of methyl acrylate has no specific attraction to the soluble palladium acetate species and yield-consuming side reactions inevitably occur.

The following examples further illustrate the process of this invention, but are not meant to limit the scope of the invention in any way.

EXAMPLE I

Step 1 — PREPARATION OF 4-IODOANISOLE

Charge 55 gallons of water and 56.2 pounds of p-anisidine to a one hundred gallon tank. With good stirring, slowly add five gallons of concentrated sulfuric acid (98%). Stir until dissolution is complete, then cool to less than 7° C. Over a 1-5 hour period, and keeping the temperature at less than 7° C., slowly add a solution of 33.3 pounds sodium nitrite and 6.6 gallons water. After the addition of the sodium nitrite is complete, stir 30 minutes at less than 7° C. Next, filter the solution through filter paper to remove any solid or tarry material. The volume of the filtered diazo solution is 73 gallons. To the filtered diazo solution, slowly add with good stirring, 1.5 pounds urea. In a separate 100 gallon tank, make up a solution of 73.3 pounds potassium iodide and 11 gallons water. Adjust the temperature of this KI solution to 25-35° C. Once the temperature of the KI solution has been adjusted to 25-35° C., begin slowly adding the filtered diazo solution to it. The addition should require 1-2 hours, keeping the temperature at 25-35° C. Some cooling will be necessary. After the addition is complete, stir at 25-35° C. for 4-6 hours. Overnight stirring is permissible. After the stirring period is complete, heat the reaction mixture to 50°-55° C. Next, add 50% NaOH until the pH is 7.5-8.0. This will require about 3.6 gallons 50% NaOH. Next, turn off the agitator and allow the phases to separate The product is on the bottom. When the phases are distinctly separated, collect the organic phase, keeping the temperature at 55-70° C. The volume of organic phase is about 6.8 gallons. Wash the organic phase with nine gallons of 55°-70° C. water, then allow the phases to separate and discard the aqueous phase. Temperature must be maintained at 55-70° C. throughout to avoid crystallization of the product. The expected yield is 97 pounds, the equivalent of 6.8 gallons, of molten 4iodoanisole.

Step 2 — PREPARATION OF 2-ETHYLHEXYL-P-METHOXYCINNAMATE

Charge 6.8 gallons of molten 4-iodoanisole from step 1, 11.4 gallons 2-ethylhexylacrylate (83.8 pounds), 7.3 gallons triethylamine (44 pounds), and 0.6 pounds of 5% palladium on carbon catalyst (dry) to a 50 gallon tank. With good agitation, begin heating. Heat to 100°-105° C. to reflux. The reflux temperature will gradually increase to about 140-145° C. The total time of reaction above 100° C. will be about 2-4 hours. After the reaction is complete, as determined by gas chromatography, cool the reaction mixture to 25°-30° C. Filter to collect the palladium catalyst and the resulting triethylamine hydroiodide salt. Wash the filtered product with 20 gallons of water to remove any soluble salt. Allow the phases to separate. The top organic product phase is ready for distillation. Its volume is about 15 gallons containing about 119 pounds of product.

Step 3 — REGENERATION OF SODIUM IODIDE

Take the bottom aqueous phase from step 2 and heat to 80°-85° C. Recycle this warm aqueous phase through the catalyst filter containing the catalyst and iodide salt until all the salt is dissolved. This will leave the palladium catalyst on the filter to be recycled to the next batch. Allow the 85° C. aqueous phase to settle. A top organic phase will separate. Collect the top organic phase (about 1-1.5 gallons) and combine it with the product filtered earlier. Cool the aqueous phase to less than 70° C. and add 50% NaOH to pH >9.5. This will require 31-34 pounds 50% NaOH. After the pH has been adjusted, adjust the temperature to 65-70° C. Then shut off the agitator and allow the phases to separate. The top triethylamine phase will be recycled to the vinylation reaction make-up; the bottom sodium iodide solution will be recycled to the iodoanisole preparation.

We claim:

1. The process of producing cinnamates having the structure

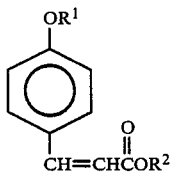

wherein $R^1$ is lower alkyl of 1 to 4 carbon atoms and $R_z$ is a branched or unbranched, substituted or unsubstituted alkyl group containing 4 to about 20 carbon atoms, comprising:

reacting an iodobenzene compound with an acrylate ester of the formula $CH_2=CHCOOR_2$ in the presence of trialkylamine and a catalyst comprising palladium on a support.

2. The process of producing 2-ethylhexyl-p-methoxycinnamate comprising reacting 4-iodoanisole with 2-ethylhexylacrylate in the presence of trialkylamine and a catalyst comprising palladium on a carbon support.

3. The process of producing 2-ethylhexyl-p-methoxycinnamate comprising
  (a) diazotizing p-anisidine to produce a diazotization product and reacting the diazotization product with an aqueous iodide solution to produce 4-iodoanisole;
  (b) reacting said 4-iodoanisole with 2-ethylhexylacrylate in the presence of trialkylamine and a catalyst comprising palladium on a carbon support to produce 2-ethylhexyl-p-methoxycinnamate and a trialkylamine-hydroiodide salt; and
  (c) recovering iodide and trialkylamine from the trialkylamine-hyiroiodide salt by reacting said salt with an alkali hydroxide.

4. The process of claim 3 wherein the iodide recovered in step (c) is recycled for use in the reaction of step (a).

5. The process of claim 3 wherein the trialkylamine recovered in step (c) is recycled for use in the reaction of step (b).

6. The process of claim 3 wherein the trialkylamine has between about one and six carbon atoms.

7. The process of claim 6 wherein the trialkylamine is triethylamine.

* * * * *

UNITED STATES PATENT AND TRADEMARK OFFICE
CERTIFICATE OF CORRECTION

PATENT NO. : 4,970,332

DATED : November 13, 1990

INVENTOR(S) : Douglas C. Caskey

It is certified that error appears in the above-identified patent and that said Letters Patent is hereby corrected as shown below:

Col. 1, line 16, change "Orc." to --Org.--.
  line 38, change "Org." to --Org.--.
  line 44, change "in situ" to --in situ--.
Col. 2, line 5, change "trialkylaminehydroiodide" to --trialkylamine-hydroiodide--.
  line 51, after "iodobenzene" insert a period --.--.
Col. 3, lines 40, 42 and 46, all occurrences, delete "C." and insert --C--.
  lines 56 and 57, change "trialkylaminehydroiodide" to --trialkylamine-hydroiodide--.
Col. 4, line 19, change "p." to --p.--.
  lines 27 and 41, all occurrences, change "C." to --C--.
  lines 55 and 56, change "trialkylaminehydroiodide" to --trialkylamine-hydroiodide--.
Col. 5, lines 9, 21 and 64, all occurrences, change "C." to --C--.
  line 11, change "trialkylaminehydroiodide" to --trialkylamine-hydroiodide--.
Col. 6, lines 7, 11, 21, 23, 35, 37, 54 and 58, all occurrences, change "C." to --C--.
  line 26, change "4iodoanisole" to --4-iodoanisole--.

UNITED STATES PATENT AND TRADEMARK OFFICE
CERTIFICATE OF CORRECTION

PATENT NO. : 4,970,332

DATED : November 13, 1990

INVENTOR(S) : Douglas C. Caskey

It is certified that error appears in the above-identified patent and that said Letters Patent is hereby corrected as shown below:

Col. 7, line 10, change "Rz" to --$R^2$--.
      line 15, change "$R_2$" to --$R^2$--.
      line 17, before "support" insert --carbon--.
Col. 8, line 13, change "hyiroiodide" to --hydroiodide--.

Signed and Sealed this

Seventh Day of April, 1992

*Attest:*

HARRY F. MANBECK, JR.

*Attesting Officer*      *Commissioner of Patents and Trademarks*